United States Patent [19]

Boesten et al.

[11] Patent Number: 5,468,901
[45] Date of Patent: Nov. 21, 1995

[54] PROCESS FOR THE PREPARATION OF OPTICALLY ACTIVE METHIONINE AMIDE

[75] Inventors: Wilhelmus H. J. Boesten; Quirinus B. Broxterman, both of Sittard, Netherlands

[73] Assignee: DSM N.V., Netherlands

[21] Appl. No.: 88,553

[22] Filed: Jul. 9, 1993

[30] Foreign Application Priority Data

Jul. 9, 1992 [NL] Netherlands .................. 9201230

[51] Int. Cl.$^6$ ................ C07C 233/05; C07C 237/06
[52] U.S. Cl. ................ 564/198; 564/192; 564/193; 564/197
[58] Field of Search ................ 564/198, 197, 564/192, 193

[56] References Cited

U.S. PATENT DOCUMENTS 4,847,412  7/1989  Boesten et al. ................ 564/164

FOREIGN PATENT DOCUMENTS 0442584   8/1991  European Pat. Off. .
1167455  10/1969  United Kingdom .
1548032   7/1979  United Kingdom .

OTHER PUBLICATIONS

Pope, W. J. et al., "Externally Compensated Tetrahydroguinaldine (Tetrahydro–2–methylquinoline) and its Optically Active components.,", Journal Chem. Soc. 2199 (1910).

Jacques, Jean et al., "Crystallization–Induced Asymmetric Transformations, " Enantiomers, Racemates, and Resolutions, pp. 369–377 (1981).

Primary Examiner—Shailendra Kumar
Attorney, Agent, or Firm—Cushman Darby & Cushman

[57] ABSTRACT

The invention relates to a process for preparing optically active methionine amide in high ee purities in which a mixture of D- and L-methionine amide or the Schiff bases thereof is at least partly converted, optionally in the presence of 0.5–4 equivalents of an aldehyde, relative to the amount of methionine amide, and water, in the presence of an organic solvent, using less than 1.2 equivalents of L- or D-mandelic acid, respectively, relative to the amount of D- or L-methionine amide, respectively, or the Schiff bases thereof, present in the mixture of D- and L-methionine amide or the Schiff bases thereof, into a salt of methionine amide and mandelic acid, a portion consisting substantially of one of the diastereoisomers of the salt is separated from the reaction mixture obtained, and the salt is converted into the optically active methionine. A high degree of optical purity is obtained. This process can be advantageously combined with a preparation of D,L-methionine amide from D,L-methionine nitrile by returning the residual methionine amide obtained after separation of the diastereomeric salt and recovery of the mandelic acid to the preparation of D,L-methionine amide where racemization of the recycled methionine amide takes place in situ. A high overall efficiency can thus obtained in spite of a relatively low efficiency of conversion into the diastereoisomeric salt, relative to the amount of D- and L-methionine amide, or the Schiff bases thereof, used.

11 Claims, No Drawings

PROCESS FOR THE PREPARATION OF OPTICALLY ACTIVE METHIONINE AMIDE

FIELD OF THE INVENTION

The present invention relates to an asymmetrical transformation process for preparing optically active methionine amide.

BACKGROUND OF THE INVENTION

A process described in Europe 442584 involves an asymmetrical transformation of amino acid amides with the aid of optically active carboxylic acids. The asymmetrical transformation of methionine amide with the aid of 2-pyrrolidone-5-carboxylic acid is mentioned as an example.

Although optically active methionine amide can be obtained with a large enantiomeric excess (ee), the described resolution of methionine amide has number of practical, yet significant drawbacks. In particular the crystal properties of the salt of methionine amide and 2-pyrrolidone-5-carboxylic acid formed as an intermediate are relatively poor. This necessarily results in relatively poor filterability and processability in general. Moreover, the 2-pyrrolidone- 5-carboxylic acid is not easily recoverable.

SUMMARY OF THE INVENTION

The present invention overcomes the practical drawbacks characteristic of the conventional process for making the desired amide while concurrently yielding the highly desired enantiomeric excess of methionine amide.

This is achieved by the present invention by using L- or D-mandelic acid as the optically active carboxylic acid in an amount less than 1.2 equivalents relative to the amount of Schiff base of D- or L-methionine amide, respectively, present in a mixture of Schiff bases of D- and L-methionine amide, and also using an amount of water that is at least equimolar relative to the amount of mandelic acid.

As a result, it has been discovered the crystal properties of the diastereoisomeric methionine amide/mandelic acid salt are unexpectedly better than those of the corresponding methionine amide-2-pyrrolidone- 5-carboxylic acid salt, which means that the methionine amide/mandelic acid salt has better filterability and processability in general.

It has also been discovered that when the process described in Europe 442584 was followed, using L- or D-mandelic acid as the optically active carboxylic acid and a racemic mixture of L- and D-methionine amide as the amino acid amide wherein the optically active carboxylic acid and the amino amide were used in virtually equimolar amounts, it was not possible to separate L- and D-methionine amide. However, unexpectedly, L- and D-methionine amide can be separated when less than an equimolar amount of L- or D-mandelic acid is used, relative to the total amount of Schiff bases of both D- and L-methionine amide, namely when less than 1.2 equivalents of L- or D-mandelic acid, relative to the amount of Schiff base of D or L-methionine amide, respectively, is present in the mixture of Schiff bases of D- and L-methionine amide.

DETAILED DESCRIPTION OF THE INVENTION

The present invention relates to an asymmetric transformation process for preparing optically active methionine amide. In this process, a mixture of D- and L-methionine amide or the Schiff bases thereof is at least partly converted, into a salt of methionine amide and mandelic acid. In this step the conversion, i.e., salt formation is conducted optionally in the presence of 0.5–4 equivalents of an aldehyde, relative to the amount of methionine amide, and water, in the presence of an organic solvent, using less than 1.2 equivalents of L- or D-mandelic acid, respectively, relative to the amount of D- or L-methionine amide, respectively, or the Schiff bases thereof, present in the mixture of D- and L-methionine amide or the Schiff bases thereof. A portion of the reaction mixture obtained during the salt formation step, which portion consists substantially of one of the diastereoisomers of the salt, is then separated from the reaction mixture obtained during the salt formation step. Thereafter the salt is converted into the optically active methionine amide. A high degree of optical purity is obtained.

This process can be advantageously combined with a preparation of D,L-methionine amide from D,L-methionine nitrile by returning the residual methionine amide obtained after separation of the diastereomeric salt and recovery of the mandelic acid to the preparation of D,L-methionine amide where racemisation of the recycled methionine amide takes place in situ. In this manner a high overall efficiency is obtained in spite of a relatively low efficiency of conversion into the diastereoisomeric salt, relative to the amount of D- and L-methionine amide, or the Schiff bases thereof, used.

It is impractical to obtain methionine amide with high e.e. when an equimolar amount of mandelic acid is used with respect to the total amount of (Schiff base of) methionine amide. However, in accordance with the present invention, an optically active methionine amide with high e.e. is obtained when a lower amount of mandelic acid is used so a lower amount of salt was formed. In other words, when adding a specific, low amount of, for instance, D-andelic acid, surprisingly, almost exclusively, the salt of D-mandelic acid and L-methionine amide crystallizes out and almost no crystallization takes place of the salt of D-mandelic acid and D-methionine amide whereas when a larger amount of mandelic acid is added, both are mixed up to give a product with low e.e. as seen from Comparative Experiment 1.

In general, less than about 1.2 equivalents, preferably 0.8–1.1 equivalents, of L- or D-mandelic acid, be used respectively, relative to the amount of Schiff base of D or L-methionine amide, respectively, present in the mixture of Schiff bases of D- and L-methionine amide. A mandelic acid/methionine amide ratio lower than about 0.8 presents the drawback of a lower degree of conversion while a ratio higher than about 1.1 affects the ee obtained in the product. With the process according to the invention, an enantiomeric excess greater than 95%, in particular greater than 98%, and even greater than 99%, can be obtained.

Instead of a mixture of the Schiff bases of L- and D-methionine amide, a mixture of L- and D-methionine amide and an aldehyde can be used. In this aspect, it is assumed that the Schiff base of methionine amide is formed in situ in an equilibrium reaction. In view of the fact that 1 equivalent of water, relative to the amount of Schiff base formed, is released in the formation of the Schiff base, no extra water need to be added to the reaction mixture in that case.

The mixture of L- and D-methionine amide or their Schiff bases can be a racemic mixture of the two enantiomers, or any other ratio of the two enantiomers can be used.

In practice, for example, a racemic or virtually racemic mixture of L- and D-methionine amide, for example a mixture of D- and L-methionine amide with an ee value of less than 20%, can be used.

The optically active mandelic acid used in the present process has a high ee value. In general, optically active mandelic acid with an ee value of more than 95% is used. The ee value is preferably more than 98%, and, in particular, is more than 99%.

The invention also relates to the novel diastereoisomeric LD and DL salts of mandelic acid and methionine amide that are obtained as intermediates. These intermediates are useful in the direct synthesis of optically active methionine amide and also optically active mandelic acid.

Examples of aldehydes that can be used in the process according to the invention are aromatic aldehydes such as, for example, benzaldehyde, anisaldehyde, o-, p- or m-nitrobenzaldehyde, o-, p- or m-chlorobenzaldehyde or aliphatic aldehydes such as, for example, isobutyraldehyde or isovaleraldehyde. Preferably, benzaldehyde is used. The amount of aldehyde to be added is about 0.5 to about 4.0 equivalents relative to the amount of methionine amide, although about 1 to 2 equivalents are preferred.

Suitable organic solvents for the process according to the invention include, among others, chlorinated hydrocarbons, such as, for example, dichloromethane, dichloroethane and chloroform, aromatic hydrocarbons, such as, for example, toluene, xylene and benzene; ethers, such as, for example, methyl tert.-butyl ether, dioxane, tetrahydrofuran and anisole, esters, such as, for example, butylacetate and ethylacetate; ketones, such as acetone, butanone and methyl isobutyl ketone, carboxylic acids, aldehydes or mixtures of thereof. The solvent is selected so that it does not enter into irreversible chemical reaction with the methionine amide, the optically active mandelic acid or the aldehyde. Preferably, a mixture of an apolar solvent that is immiscible with water and a small amount of a polar solvent, for example a lower alcohol such as methanol or ethanol, is used as the solvent. Suitable examples of such mixtures are methyl tert.-butyl ether (MTBE) and methanol, toluene and methanol, and methyl isobutyl ketone (MIBK) and methanol.

The pressure at which the process according to the invention is carried out is not critical, and can, for example, range from about 0.01 to 1 MPa. Preferably, the process is carried out at atmospheric pressure. The temperature can vary within wide limits such as, for example, between about 20° C. and about 90° C. The optimum temperature at which the process according to the present invention is carried out is partly a function of balancing the advantages of a higher reaction rate at higher temperatures versus, a lower solubility of the diastereoisomeric salt at a lower temperature. The reaction time is usually 0.1–8 hours, although 0.1–2 hours is preferred.

The slurry concentration of the diastereoisomeric salts at the end of the reaction is usually about 5 to about 30 wt. %, and is preferably about 10 to about 20 wt. %.

The optically active methionine amide can be obtained from the separated diastereoisomeric salt by dissolving the salt in a mixture of water and a virtually equimolar amount of mineral acid such as hydrochloric acid, sulphuric acid, nitric acid or phosphoric acid, and extracting the optically active mandelic acid with the aid of an extraction agent. Suitable extraction agents include, for example, ethers, alcohols, ketones or esters such as methyl tert.-butyl ether, methyl isobutyl ketone, ethyl acetate, butyl acetate or amyl alcohol.

The optically active methionine amide obtained can be converted into the corresponding amino acid in a known manner such as, for example, via hydrolysis with the aid of an excess amount of diluted mineral acids such as hydrochloric acid, sulphuric acid, nitric acid or phosphoric acid. The hydrolysis is preferably carried out at about 60° C. to about 100° C., and in particular, at 85°–95° C. Optically active methionine is used in, for example, infusions. Infusions are described in, for instance, *Ullman's Encyclopedia of Industrial Chemistry*, A2: 75–76, 83, 86–87 (1985), the disclosure of which incorporated herein by reference. Optically, active methionine is also useful in the synthesis of pharmacologically active compounds.

The diastereoisomeric salt of the reaction mixture is usually separated before the hydrolysis and further treatment.

Mixtures of D- and L-methionine amide can be obtained in a manner known per se. Preferably, the process according to the invention is used in combination with a process in which the Schiff bases of D,L-methionine amide are prepared by reacting D,L-methionine nitrile with at least 1 equivalent of an aldehyde or ketone, for example benzaldehyde, and a base, preferably a strong base, in an organic solvent, as described, for example, in GB 1,548,032 (1979), the disclosure of which is incorporated herein by reference. Under these conditions racemisation of the Schiff base of methionine amide was found to take place. In this embodiment, the process according the invention comprises returning the filtrate containing the residual Schiff base of methionine amide, obtained after crystallisation and filtration of the diastereoisomeric methionine amide/mandelic acid salt and removal of the residual optically active mandelic acid such as by means of, for example, basic water extraction, to the D,L-methionine amide preparation reaction. Moreover, the optically active mandelic acid obtained can be re-used in the present process, such as by recycling it to step involving conversion of the amide or Schiff bases. An added advantage is that the optical purity of the mandelic acid gradually increases in the subsequent cycles. The relatively low degree of conversion with respect to the amount of methionine amide or the Schiff base thereof in the formation of the methionine amide/mandelic acid salt in the reaction according to the invention, as a result of the use of less than an equimolar amount of L- or D-mandelic acid, is, compensated for completely.

The disclosures of Europe 442–584 and Jacques et al, Enantiomers, Racemates and Resolutions, pgs. 369 ff. (John Wiley 1981) are incorporated herein by reference.

The invention is now further explained with reference to the following non-limiting examples.

EXAMPLES

Each experiment was carried out under a nitrogen atmosphere. The products obtained in the Examples were analyzed by thin layer chrmotography ("tlc"). In the tlc technique a Merck 60 F 254 silica gel was used as a carrier. The tlc detection methods were: U.V. (short wave) and ninhydrin. The three tlc eluents and the volume ratios in which they were used are:

```
A  CHCl3 — CH3OH — NH4OH (25 wt. %)
   60        45        20

B          sec. butanol - formic acid - water
   75                       15            10

C  n-butanol - acetic acid - ethylacetate - water
   1              1              1            1
```

The selectivity (enantiomeric purity) is defined as follows:

$$\text{selectivity} = 50\% + \frac{50 \times [\alpha]_D^{20}}{\max. [\alpha]_D^{20}} \ \% \text{ enantiomer}$$

The maximum specific rotation of D-methionine amide. HCl is described in U.S. Pat. No. 4,847,412 as: $[\alpha]_D^{20} = -18.2°$ (c=1.0; water).

The maximum specific rotation of L-methionine is given in *J. Chem. Soc.*, 97:2199 (1910) as $[\alpha]_D^{20} = +23.4°$ (c=3.0; 1.0N hydrochloric acid).

COMPARATIVE EXPERIMENT

Equimolar resolution is shown in this comparative experiment.

0.1 mole (23.6 g) of D,L-N-benzylidenemethionine amide (Schiff base of benzaldehyde and D,L-methionine amide), 0.1 mole (15.2 g) of D-mandelic acid, 250 ml of n- dibutylether, 10 ml of methanol and 2 ml of water (0.11 mole) were stirred for 3 hours at a temperature of 71° C. in a reaction flask fitted with a stirrer, a thermometer and a reflux condenser. After cooling to 20° C. the salt obtained was filtered and rinsed through a glass filter using 3×30 ml of n-di-butyl ether. The salt yield was 26.9 grams.

3.0 g (0.01 mole) of the salt obtained was dissolved in a mixture of 2 ml of water, 3 ml of 36 wt. % hydrochloric acid and 5 ml of acetone at a temperature of 50° C. With stirring, 100 ml of acetone was then added to this clear solution. The specific rotation of the dried methionine amide. HCl obtained after filtration and rinsing through a glass filter (3× 10 ml of acetone) (yield=1.5 g; tlc pure) was: $[\alpha]_D^{20} = +1.0°$ (c=1.0; water); selectivity=52.7% L-enantiomer.

EXAMPLE I

Resolution with the aid of 0.5 equivalent D-mandelic acid is shown in Example I.

0.1 mole (23.6 g) of D,L-N-benzylidenemethionine amide, 0.05 mole (7.5 g) of D-mandelic acid, 90 ml of methyl isobutyl ketone, 10 ml of methanol and 0.9 ml of water (0.05 mol) were stirred for a period (t) of 15 minutes at a temperature of 50° C. in a reaction flask fitted with a stirrer, a thermometer and a reflux condenser.

The diastereoisomeric salt obtained after cooling to 30° C. was filtered and rinsed through a glass filter using 3×20 ml of methyl isobutyl ketone. The amount of salt obtained after drying was 8.2 g, which corresponds to an efficiency (E) of 54.7%, relative to the amount of L-methionine amide used. The specific rotation of the tlc-pure methionine amide.HCl prepared from this diastereoisomeric salt was: $[\alpha]_D^{20} = +17.9°$ (c=1.0; water); selectivity=99.2% L-enantiomer (L).

EXAMPLES II–V

Example I was repeated. The data for Examples II–V are reported in Table I.

BIMA=D,L-N-benzylidenemethionine amide
MA=mandelic acid
BA=benzaldehyde
MTBE=methyl tert.-butyl ether.

TABLE I

| EX. | BIMA mole | MA mole | solvent comb. | t min. | T °C. | $[\alpha]_D^{20}$ | sel. % | E % |
|---|---|---|---|---|---|---|---|---|
| II | 0.2 | 0.1 (L) | 210 ml MTBE 40 ml CH₃OH 2 ml H₂O | 45 | 50 | -17.8° | 99.2 (D) | 45.7 |
| III | 0.1 | 0.05 (D) | 90 ml MTBE 9 ml CH₃OH 1 ml H₂O | 20 | 45 | +16.7° | 95.9 (L) | 64.0 |
| IV | 0.2 | 0.1 (D) | 90 ml MTBE 10 Ml CH₃OH 2 ml H₂O | 10 | 45 | +17.8° | 99.2 (L) | 68.7 |
| V | 0.1 | 0.05 (L) | 45 ml MTBE 5 Ml BA 1 ml H₂O | 10 | 50 | -11.7° | 82.1 (D) | 72.0 |

EXAMPLE VI

Resolution with the aid of less than 0.5 equivalent D-mandelic acid followed by acid hydrolysis of L-methionine amide to L-methionine is shown in Example VI.

2.7 mole (637 g) of D,L-N-benzylidenemethionine amide, 1.25 mole (190 g) of D-mandelic acid, 1150 ml of methyl tert.-butyl ether, 200 ml of methanol and 23 ml of water (1.25 mol) were stirred for 1 hour at 50° C. in a reaction vessel fitted with a stirrer, a thermometer and a reflux condenser. The diastereoisomeric salt obtained after cooling to 30° C. was filtered and rinsed through the glass filter using 5×200 ml of 85 vol. % methyl tert.-butyl ether/methanol.

The yield obtained after drying was 212 g, which corresponds to an efficiency of 52.4%, relative to the amount of L-methionine amide used. 208 g (0.69 mole) of diastereoisomeric salt was dissolved in a mixture of 210 ml of water and 25 ml of 96 wt. % sulphuric acid (0.45 mol) and then the D-mandelic acid was removed by means of extraction using 4×300 ml of methyl tert.-butyl ether at a temperature of 30° C.

90 ml of 96 wt. % sulphuric acid was added to the aqueous L-methionine amide.H₂SO₄ solution and this was followed by hydrolysis to L-methionine in 3 hours, with stirring, at 90° C. The acid hydrolysate was neutralized using 250 ml of 25 wt. % ammonia to a pH of 6, with stirring, at a temperature of 60°–80° C. The L-methionine obtained after cooling to 25° C. was filtered and then rinsed through a glass filter using 2×100 ml of water (saturated with L-methionine) and 4×75 ml of 70 vol. % methanol/water.

The yield of tlc-pure L-methionine obtained after drying was 90.3 g, which corresponds to an efficiency of 88.2%. The specific rotation of the L-methionine is: $[\alpha]_D^{20} = +22.9°$ (c=3.0; 1.0N hydrochloric acid), selectivity=99.0%. Literature: *J. Chem. Soc.*, 97:2199 (1910); $[\alpha]_D^{20} = +23.4°$ (c=3.0; 1.0N hydrochloric acid).

What we claim is:

1. A process for preparing optically active methionine amide comprising:
   (a) converting, at least in part, a mixture of the Schiff bases of D- and L-methionine amide with an optically active L- or D-mandelic acid into a salt of the methionine amide and the carboxylic acid in the presence of water and an organic solvent wherein the amount of L- or D-mandelic acid, respectively, is less than about 1.2 equivalents, relative to the amount of the Schiff base of D- or L-methionine amide, respectively, present in the mixture of Schiff bases of D- and L-methionine amide, and the amount of water used is at least equimolar relative to the amount of mandelic acid,
   (b) separating a portion consisting substantially of one of the diastereoisomers of said salt from the reaction mixture obtained in (a); and
   (c) converting the salt into the optically active methionine amide.

2. A process for preparing optically active methionine amide comprising:
   (a) converting, at least in part, a mixture of L- and D-methionine amide with an optically active L- or D-mandelic acid into a salt of the methionine amide in the presence of 0.5 to 4 equivalents of an aldehyde, relative to the amount of methionine amide, water and an organic solvent, wherein the amount of L- or D-mandelic acid, respectively, is less than 1.2 equivalents, relative to the amount of D- or L-methionine amide, respectively, present in the mixture of D- and L-methionine amide;
   (b) separating a portion consisting substantially of one of the diastereoisomers of said salt from the reaction mixture obtained from (a); and
   (c) converting the salt into the optically active methionine amide.

3. A process according to claim 2, wherein the molar ratio of the amount of the L- or D-methionine amide in the mixture of L- and D-methionine amide is about 2:1 to the amount of the optically active L- or D-mandelic acid.

4. A process according to claim 2, wherein the amount of aldehyde is about 1 to 2 equivalents relative to the amount of methionine amide.

5. Process according to claim 2, wherein 1 to 2 equivalents of an aldehyde, relative to the amount of methionine amide, are used.

6. Process according to claim 2, wherein a racemic or virtually racemic mixture of L- and D-methionine amide or their Schiff bases is used.

7. Process according to claim 1, wherein about 0.8 to about 1.1 equivalent of L- or D-mandelic acid, respectively, relative to the amount of D- or L-methionine amide, respectively, or of the Schiff bases thereof, present in the mixture of D- and L-methionine amide or the Schiff bases thereof.

8. Process according to claim 2, wherein the mandelic acid has an ee of greater than 98%.

9. Process according to claim 2, wherein the organic solvent comprises a mixture of an apolar solvent that is not miscible with water and a polar solvent.

10. Process according to claim 2, wherein the mixture of the Schiff bases of L- and D-methionine amide in (a) is at least partly prepared by reacting a mixture of L- and D-methionine nitrile in the presence of at least 1 equivalent of an aldehyde or a ketone, relative to the amount of methionine nitrile, in the presence of a base in an organic solvent and, after (b) and after removal of remaining optically active mandelic acid from the reaction mixture, recycling the reaction mixture to (a).

11. A process according to claim 1 further comprising hydrolyzing the methionine amide to methionine.

* * * * *